(12) United States Patent
Reed (10) Patent No.: US 9,526,547 B2
(45) Date of Patent: Dec. 27, 2016

(54) BONE SCREW

(71) Applicant: Gary Jack Reed, Turlock, CA (US)

(72) Inventor: Gary Jack Reed, Turlock, CA (US)

(73) Assignee: RGT SCIENTIFIC INC., Turlock, CA (US)

( * ) Notice: Subject to any disclaimer, the term of this patent is extended or adjusted under 35 U.S.C. 154(b) by 0 days.

(21) Appl. No.: 13/815,504

(22) Filed: Mar. 6, 2013

(65) Prior Publication Data

US 2014/0257409 A1    Sep. 11, 2014

(51) Int. Cl.
*A61B 17/86* (2006.01)
*A61B 17/16* (2006.01)

(52) U.S. Cl.
CPC ......... *A61B 17/864* (2013.01); *A61B 17/8625* (2013.01); *A61B 17/1655* (2013.01); *A61B 17/863* (2013.01); *A61B 17/8635* (2013.01)

(58) Field of Classification Search
CPC . A61B 17/86; A61B 17/8605; A61B 17/8615; A61B 17/862; A61B 17/8625; A61B 17/863; A61B 17/8635; A61B 17/864; A61B 17/8645; A61B 17/865; A61B 17/866; A61B 2017/8655
USPC ................................................. 606/300–321
See application file for complete search history.

(56) References Cited

U.S. PATENT DOCUMENTS

| | | | | |
|---|---|---|---|---|
| 4,144,795 A * | 3/1979 | Gutshall | .................. | 411/413 |
| 4,334,814 A * | 6/1982 | McKewan | .................. | 411/311 |
| 4,600,224 A * | 7/1986 | Blose | .................. | 285/334 |
| 4,810,149 A * | 3/1989 | Lee et al. | .................. | 411/411 |
| 5,098,435 A * | 3/1992 | Stednitz et al. | .................. | 606/916 |
| 5,129,901 A * | 7/1992 | Decoste | .................. | 606/65 |
| 5,156,616 A * | 10/1992 | Meadows et al. | .................. | 606/232 |
| 5,727,943 A * | 3/1998 | Beaty et al. | .................. | 433/174 |
| 6,306,140 B1 * | 10/2001 | Siddiqui | .................. | 606/315 |
| 6,315,564 B1 * | 11/2001 | Levisman | .................. | 433/174 |
| 6,402,757 B1 * | 6/2002 | Moore et al. | .................. | 606/80 |
| 6,635,059 B2 * | 10/2003 | Randall et al. | .................. | 606/916 |
| 6,997,927 B2 * | 2/2006 | Jackson | .................. | 606/273 |
| 7,037,309 B2 * | 5/2006 | Weil et al. | .................. | 606/304 |
| 7,198,488 B2 * | 4/2007 | Lang et al. | .................. | 433/174 |
| 8,118,849 B2 * | 2/2012 | Wahl et al. | .................. | 606/315 |
| 8,128,671 B2 * | 3/2012 | Taylor | .................. | 606/315 |
| 8,394,132 B2 * | 3/2013 | Lewis et al. | .................. | 606/301 |
| 8,414,628 B2 * | 4/2013 | Melkent | .................. | 606/309 |
| 8,602,781 B2 * | 12/2013 | Reed | .................. | 433/174 |
| 8,636,783 B2 * | 1/2014 | Crall et al. | .................. | 606/308 |
| 8,771,324 B2 * | 7/2014 | Black et al. | .................. | 606/305 |
| 2003/0088251 A1 * | 5/2003 | Braun et al. | .................. | 606/73 |

(Continued)

*Primary Examiner* — Christian Sevilla
*Assistant Examiner* — Eric S Gibson
(74) *Attorney, Agent, or Firm* — Bacon & Thomas, PLLC (57) ABSTRACT

A threaded fastener for embedment into bone is disclosed. Threads are formed on cylindrical stock. The thread pattern features upper and lower surfaces. The upper surface includes (in section) two facets which intersect to form a "V" shaped contour and a lower surface which is undercut below an upper facet nearest a root of the fastener thread. The fastener includes a self-tapping cutter at a distal extremity and a driving head at its proximal extremity. The cylindrical stock contemplates two variants: it may be hollow from the proximal end to the self-tapping cutter or from the self-tapping cutter to its distal end. The self-tapping cutter is configured to feed bone shards into the hollow.

5 Claims, 8 Drawing Sheets

(56) References Cited

U.S. PATENT DOCUMENTS

| | | | |
|---|---|---|---|
| 2003/0187447 A1* | 10/2003 | Ferrante et al. | 606/73 |
| 2005/0101961 A1* | 5/2005 | Huebner et al. | 606/72 |
| 2005/0266381 A1* | 12/2005 | Abarno | 433/173 |
| 2007/0233123 A1* | 10/2007 | Ahmad et al. | 606/73 |
| 2008/0234763 A1* | 9/2008 | Patterson et al. | 606/315 |
| 2008/0286720 A1* | 11/2008 | Reed | 433/174 |
| 2009/0240291 A1* | 9/2009 | Gorek | 606/316 |
| 2010/0211113 A1* | 8/2010 | Olson et al. | 606/301 |
| 2010/0268285 A1* | 10/2010 | Tipirneni et al. | 606/309 |
| 2010/0312245 A1* | 12/2010 | Tipirneni et al. | 606/62 |
| 2011/0213426 A1* | 9/2011 | Yedlicka et al. | 606/309 |
| 2011/0295319 A1* | 12/2011 | Duplessis et al. | 606/264 |
| 2012/0041395 A1* | 2/2012 | Sweeney | 604/272 |
| 2012/0089195 A1* | 4/2012 | Yedlicka et al. | 606/304 |
| 2012/0116459 A1* | 5/2012 | Nottmeier | 606/279 |
| 2013/0231708 A1* | 9/2013 | Melkent | 606/308 |
| 2013/0237813 A1* | 9/2013 | Beyar et al. | 600/424 |
| 2014/0058460 A1* | 2/2014 | Reed | 606/312 |
| 2014/0094859 A1* | 4/2014 | Reed | 606/312 |

* cited by examiner

BONE SCREW

FIELD OF THE INVENTION

A fastener for embedment in bone is constructed to be easily inserted and reliably retained in the bone.

BACKGROUND OF THE INVENTION

Surgical procedures involving fasteners on skeletal structure presently suffer from several common frailties. One is the inability to accurately orient the fastener during insertion to keep the fastener from wandering. Bone interiors have a sponge like (cancellous) texture. Even with a predrilled pilot hole, fasteners still frequently skew off the axis of the pilot hole, making it difficult to register the fastener at its distal end with another instrumentality.

Another frailty is the failure to provide a reliable thread portion that engages the bone of the patient in a manner which retards its working loose. Bone is a remarkable structure which varies both in hardness and elasticity as a function of both age and location. Loads on the fastener must accommodate not only these constraints but also the dynamics of forces generated by the patient in daily activities.

The buttress thread is presently the industry standard. Unfortunately, buttress threads are suitable for use only where load forces on the fastener are applied in one direction. (Bhandari, Design of Machine Elements (2007), page 204). Where the load forces are multidirectional or not unidirectional and axial, failure can occur. One manifestation of buttress thread failure is "toggling" where the fastener works on the bone and enlarges the hole within which the fastener resides.

Yet another frailty related to high insert torque makes it impossible to insert the screw through bone fragments without it grabbing the fragment and causing it to rotate with the screw causing significant trauma to soft tissues and a failed fixation of the fragment.

In an attempt to offset the multiple problems of buttress threads, it is common practice to design the buttress thread profile to increase retention by increasing friction. Increased friction leads to elevated temperatures during insertion, potentially damaging bone tissue. A temperature excursion greater than 116 degrees Fahrenheit (47 degrees Celsius) at the insertion site causes osteonecrosis which cannot be repaired and which the body cannot heal. And, even worse, excess heat compromises the fastener's ability to remain in place since the bone has died at the screw thread interface. As a consequence, some procedures rely on liquid cooling at the site during the drilling/insertion procedure, but, even then, the process generates so much heat that the heat generating tool can be too hot to touch because the liquid cooling is merely topical.

Since the only variables (thread pitch, crest and root diameters) in the buttress thread design are interrelated, improving retention increases friction and insertion torque, resulting in heat generation and impairing the surgeon's ability to feel the insertion torque of the fastener in a meaningful way. This still leaves the fundamental problem of the thread's inability to withstand multidirectional forces unaddressed, while creating several new problems.

The surgeon has no tactile feedback when inserting the fastener. The buttress fastener is harder to start and is prone to stripping, especially when used in conjunction with a plate. The wedge shaped buttress thread induces an outwardly radial force, perpendicular to the fastener's long axis, which increases the probability the bone will split or crack, making a procedure much more difficult, if not impossible. The buttress threaded fastener can wander during insertion, making its registry with an instrumentality at the distal end of the fastener a recurring problem. Wandering away from the pilot hole often results in cutting new threads in an unintended location or stripping out the pilot hole which retards healing and actually induces trauma; and, where there is a temperature excursion above 116 degrees Fahrenheit, it can also cause osteonecrosis of the adjacent bone.

The present invention's thread geometry minimizes insertion force. This allows the surgeon tactile feedback and reduces the effort required to deploy the fastener. This, in conjunction with chip disposal, a centering pilot, and improved thread cutting features keep friction low, the fastener aligned and directed from wandering away from the preferred path.

The distal end of many fasteners includes an area (cutting flute) designed to help cut through bone, defining a "self-tapping" fastener. Buttress thread fastener's self-tapping features a flute that is straight or at least close to in-line with the long axis of the screw. That is, as the fastener is advanced, the cutting edges send the bone chip towards the head of the fastener which is into the path of the helical threads. This bone debris accumulates along the thread teeth and increases insertion torque and friction which therefore generate additional heat. The debris also makes the fastener harder to insert and provides a poor interface with the bone and the fastener.

In the present invention, the cut chips curl away from the cutting edges (located on one or more threads at the distal end) and are fed downwardly into a hollow of the fastener because of a chamfer at thread interruptions which define cutting surfaces or flutes. That is, as the fastener advances, the flute forces the chips downwardly into a hollow of the screw. This results in exact clearance between the fastener and the portion of the bone being formed as "bone teeth" (that portion which engages the threaded fastener). The interface between the bone and fastener is therefore substantially free of the cuttings and provides healthier bone tissue adjacent the fastener to prevent additional trauma to the bone.

Another problem associated with buttress style threads is that the area between threads of the fastener is the only site of anchoring in the bone, and because of the design constraints associated therewith, this site is difficult to optimize. Stated alternatively, the metal of the fastener is orders of magnitude stronger than the retaining bone so that when failure occurs, it always involves bone trauma.

The present invention maximizes the bone being engaged while minimizing the fastener's thread, something impossible to do with a buttress thread and other common threads and common manufacturing processes. The result is less bone trauma and less bone removed to increase bone strength to retain the fastener better.

This invention discards conventional thinking and manufacturing processes in the pursuit of new and desirable functions that can be achieved from the thread profile.

Heretofore manufacturers have adopted a simple and very fast manufacturing process that produce screws that function no better than common wood screws.

BRIEF SUMMARY OF THE INVENTION

The present invention reflects results of applicant's ongoing research in threaded fasteners specialized for use in bone. Five thread patterns are disclosed, all of which function by "interlocking" with adjacent bone into which the fastener is embedded. The thread patterns may extend along the entire exterior length of the fastener or partially along the length. Two variations of a self-tapping cutter are disclosed: both of which feed cut bone shards into a hollow interior of the fastener: one cutter feeds shards into the interior towards a proximal end and another cutter feeds shards into a distal end. Thus, the interior is hollow either from the cutter towards the proximal end or from the cutter to its distal end. A pilot is located on the distal end. The self-tapping cutter is spaced a short distance from the pilot and the threads defining the cutter area decrease in crest diameter approaching the distal end of the fastener. Typically, one or more threads taper and the drawings show three such threads.

The instant invention addresses various skeletal components with fasteners in ways heretofore unattainable with an improved thread pattern which provides greater retention of bone structure and minimal damage to bone adjacent the fastener.

This invention produces a bone screw thread design that can be modified in many independent ways to produce different capabilities and functions that can contribute to better grip, greater resistance to pull-out, lower cutting and insertion pressure which reduces site temperature and causes less damage to the bone in the process. These features provide better feel for the surgeon installing the screws to prevent stripped threads, better clamping force, better fixation, and ultimately shorter healing time.

The fastener is formed using a CNC manufacturing process which utilizes single-point threading in conjunction with multiple form cutting tools with different shapes and following different paths to create thread features formed by independently programmable successive cutting moves, each distinct from the others. This means that the tooth height, thickness and spacing can now each be modified independently to produce different characteristics and capabilities to greatly improve both the procedure when the screw is installed into the bone and the performance of the screw in situ.

While the method that is being disclosed forms threads of greater complexity in the process, in a production setting it is only possible because of CNC machine tools and the ability to program sequential, independent cutting moves to create unique features unknown in the prior art.

Bone fixation is very complicated because the breaks are found in an infinite variety of shapes and locations. Fasteners embedded in bone need to minimize bone trauma and removal while maximizing retention in a dynamic environment. The benefits derived from these new thread designs and a method to produce them will be very significant to the industry and patients.

OBJECTS OF THE INVENTION

Accordingly, it is a primary object of the present invention to provide an orthopedic fastener structure and method.

A further object of the present invention is to provide an improved threaded portion therefore.

A further object of the present invention is to provide an improved threaded portion which minimizes bone trauma, resists failure and is easy to install.

A further object of the present invention is to provide a fastener which can accommodate a plurality of different angles of attack when addressing a skeletal structure.

Viewed from one vantage point, it is an object of the present invention to provide an orthopedic fastener formed by independently modifying tooth height, thickness and spacing, thus altering said faster's characteristics and capabilities.

Viewed from another vantage point, it is an object of the present invention to provide an orthopedic fastener formed by: independently modifying tooth height, thickness and spacing, thus altering said fastener's characteristics and capabilities, whereby pitch and major and minor tooth thread diameters are independently variable to facilitate matching fastener thread profiles with corresponding bone tooth profiles as a function of bone density and site of fastener deployment to improve fastener purchase and increase resistance to pull out forces.

Viewed from the previous vantage point, it is an object of the present invention to provide a fastener further including forming a chip cutting flute at a distal end thereof, said chip cutting flute having leading cutting edges defining a cutting thread pattern disposed on said distal end and spiraling helically on the fastener, said thread pattern disposed on said remainder of the fastener defining a substantially non cutting, interlocking thread pattern whereby said cutting flute forms the interlocking thread pattern in the bone thereby reducing friction upon fastener insertion and minimizing heat buildup while providing greater sensitivity during fastener installation, reducing installation torque and possible misalignment which otherwise causes unnecessary bone removal and thread stripping while resisting breaking loose bone fragments during installation.

Viewed from the previous vantage point, it is an object of the present invention to provide a fastener further formed by disposing the interlocking thread pattern spirally along the fastener, interrupted by a substantially cylindrical fastener shaft such that said fastener shaft defines a cylindrical wall spiraling along a length of said fastener and interrupted by said interlocking thread pattern, whereby said interlocking pattern retards toggling of the fastener and minimizes radial forces while resisting multidirectional forces and bending moments which otherwise could cause fastener upheaval, and the cylindrical shaft defines a contact surface for bone devoid of sharp surfaces which would cause pressure points.

Viewed from the previous vantage point, it is an object of the present invention to provide a fastener further forming an abutment surface adjacent a proximal end of said fastener, defining an impediment to further fastener advancement and means to induce clamping of said fastener in an orthopedic environment.

Viewed from a previous vantage point, it is an object of the present invention to provide a fastener further forming an interference fit adjacent a proximal end of said fastener, defining an impediment to further fastener advancement and means to induce clamping of the fastener in an orthopedic environment.

Another vantage point contemplates an orthopedic fastener, comprising, in combination: a shaft having a proximal end provided with means for advancing said fastener and means for impeding fastener advancement, said shaft having a thread pattern providing interlocking means wound about said shaft, said thread pattern interrupted by intervening smooth, cylindrical walls of said shaft, a thread forming means on a distal end of said shaft, said thread forming means having a thread pattern a mirror image of and opposite from said fastener thread pattern having said interlocking means, and a pilot at said distal end of said shaft adjacent said thread forming means, said thread forming means including means to store bone fragments interiorly and away from threads of said fastener.

These and other object will become clearer when considering the following.

DESCRIPTION OF PREFERRED EMBODIMENTS

Figure 1:
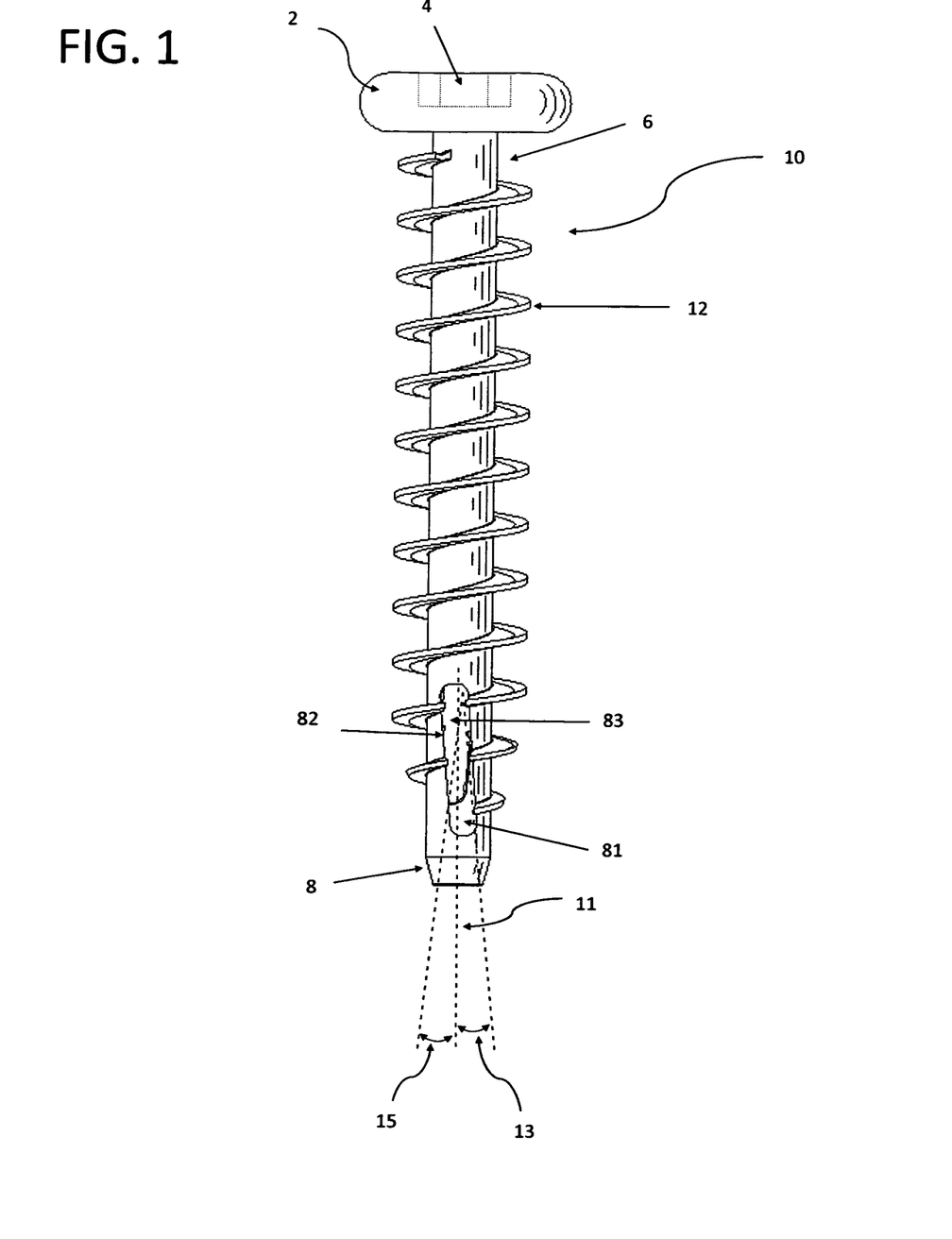
FIG. 1 shows a fastener with a thread along the cylindrical shaft.
Figure 8:
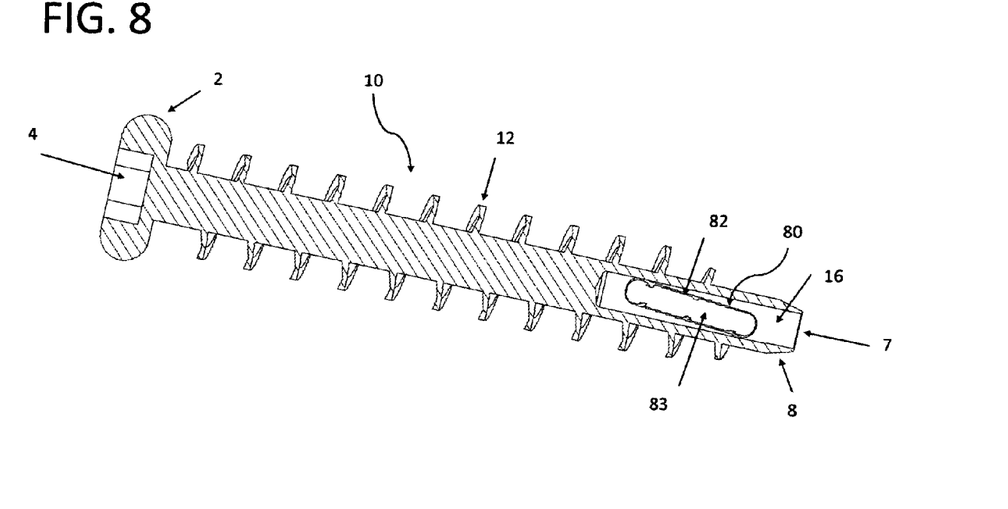
FIG. 8 is a sectional view taken along the long axis of the fastener showing a hollow serving as a chip repository at a distal end.
Figure 9:
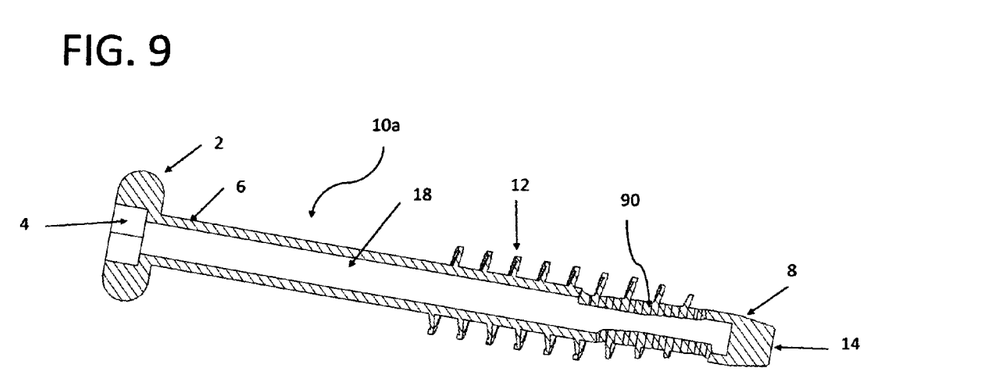
FIG. 9 is another longitudinal sectional view showing the hollow at the proximal end.

FIG. 1 depicts a plan view of a bone fastener 10 have a full flight of threads along its length; FIG. 8 shows the fastener 10 in section and FIG. 9 shows a modified fastener 10a having threads 12 only partially deployed and located at a distal end 14, adjacent pilot 8. The fastener shaft 6 above this threaded portion is smooth and cylindrical, as it is between all intervening threads. That is, the space between adjacent threads is cylindrical, thereby avoiding potential pressure points with adjacent bone. The fastener includes a head 2 at a proximal end that includes an instrumentality to facilitate fastener deployment, illustrated here as a female socket 4 to engage a complementally formed driving tool.

FIGS. 8 and 9 also display two variations of the fastener 10, 10a internally. FIG. 8 reflects a hollow bore 16 in communication between and open distal end 7 and a lower bore repository 80 located in a cylindrical periphery circumscribing and defining the bore 16. This bore 80 is adjacent to and coextensive with the cutting flutes. FIG. 9 reflects a hollow bore 18 extending from the proximal end and passing through the head 2 via socket 4 down to an upper bore repository 90 located on a cylindrical portion of the distal end adjacent cutting flutes. In this embodiment, it is preferred to close the distal end with a wall 14 defining a blind bore. The thread length shown in FIGS. 8 and 9 could be transposed such that the abbreviated thread of FIG. 9 could feed a lower bore repository shown in FIG. 8 and the full thread 12 of FIG. 8 could feed an upper bore repository 90 as shown in FIG. 9.

In both fasteners, the distal end has a conical taper 8 diverging from the distal terminus and enlarging towards the cutting flutes where its diameter is equal to the shaft diameter. This taper discourages the fastener from wandering from a predrilled pilot hole.

When the FIG. 9 repository 90 is selected, it is possible to remove bone shards from the bore 18 and introduce additives into the bore 18 for dispensation about the bone/thread interface via the opening of the repository 90 that is adjacent the cutting flutes. Examples of additives include, but are not limited to: medicines, bone growth stimulants, and other substances having beneficial value.

FIGS. 3 through 7 exemplify five thread forms having geometry optimized for retention in bone irrespective of the bone characteristics (e.g. cortical, cancellous, osteoporotic, variable density, variable elasticity, etc.). Upper inner root flanks (or facets) (32, 42, 52, 62 and 72) and upper outer flanks (33, 43, 53, 63 and 73) work in conjunction with lower undercut inner root flanks (34, 44, 54, 64 and 74) to provide primary thread retention in the adjacent bone. The conjunction of upper flanks form a substantially "V" shaped profile (when view in section) which centers and locates the bone by virtue of the crotch of the "V" and directs all loads imposed on the screw/bone interface to remain centered in place. In conjunction with the lower inner undercut root flank, all loads are resisted primarily by these three flanks and thwart migration of the fastener, preventing it from working loose. The lower inner root flank traps bone between it, the shaft and the adjacent upper flanks by threaded retention.

All of the undercut lower root flanks—by definition of undercut—angle downwardly, from root attachment out and down towards the distal end. Because the upper root flanks also declinate downwardly towards the distal end, these two root flanks when viewed jointly tend to converge as they extend away from the root.

Each thread pattern includes a lower, outer flank: 35, 45, 55, 65 and 75. This lower outer flank extends from the lower undercut root flank. FIGS. 3 through 7 reflect various angulations at the juncture of these lower flanks. Facets 45, 55, 65 and 75 appear substantially perpendicular to the long axis 11 of the fastener, while flank facet 35 is canted towards the proximal end of the fastener.

Figure 3:
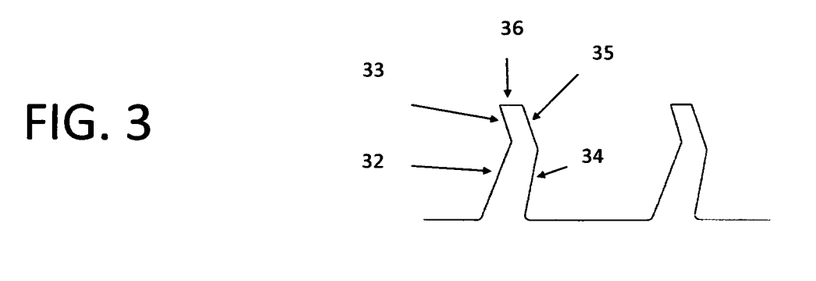
FIG. 3 shows a first tooth profile in section.
Figure 3A:
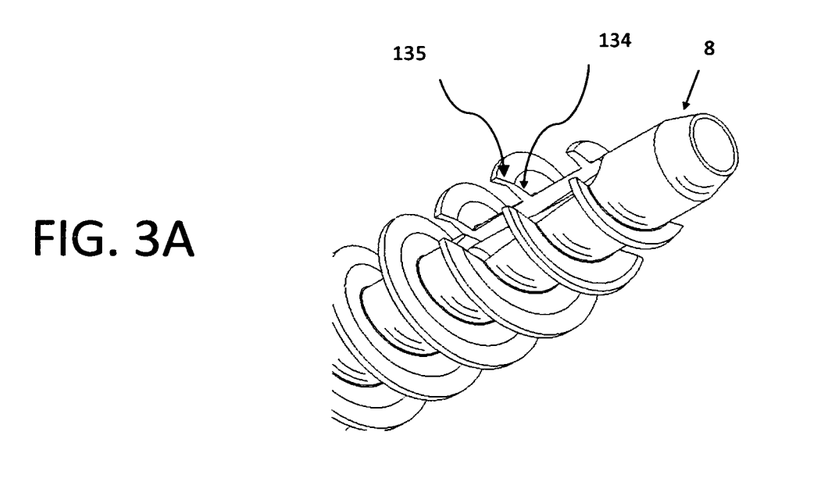
FIG. 3A shows one perspective of the FIG. 3 cutting flute.
Figure 3B:
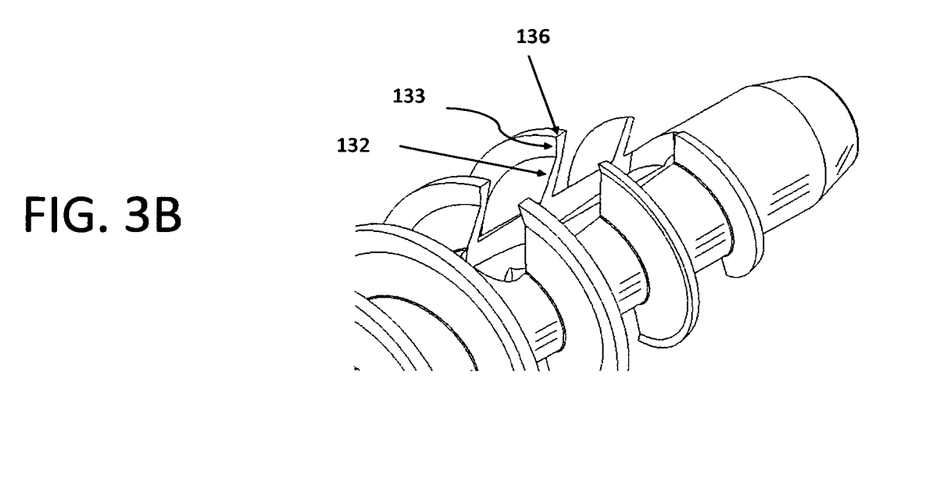
FIG. 3B shows a second perspective.

FIG. 3 shows upper 33 and lower 35 outer flanks terminating at an outboard extremity in a crest diameter 36, whose thickness is subject to modification from an appreciable thickness—as shown—to a minimal thickness approaching a thin edge, controlled by the machining process. As shown, crest 36 appears parallel to the long axis 11 (FIG. 1) of the fastener.

Figure 4:
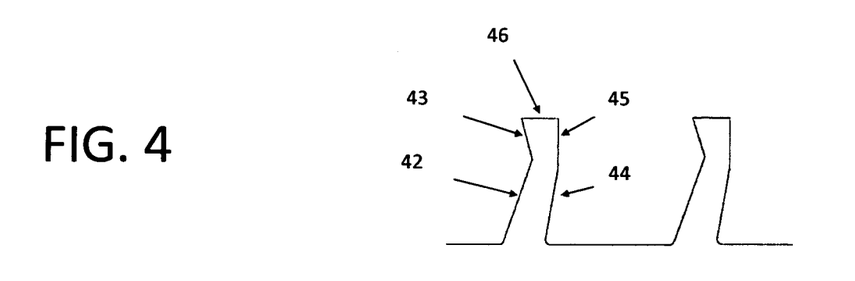
FIG. 4 shows a second tooth profile in section.

Similarly, crests 46, 56, 66 and 76 all appear parallel to the fastener long axis 11. In FIG. 4 an outermost portion of upper flank 43 registers with proximal edge of crest 46 while lower flank 45 registers with the distal edge of crest 46. Comparing FIGS. 3 and 4, the proximal angulation of lower outer flank 35 represents a thinning of the material of the crest 36.

Figure 5:
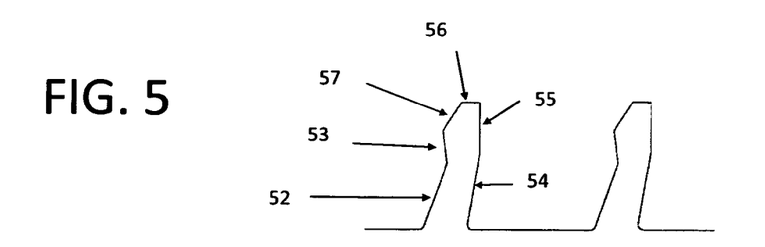
FIG. 5 shows a third tooth profile in section.

FIG. 5 includes a further upper flank 57 extending between an outer most portion of upper flank 53 and a proximal edge of crest 56. A distal edge of crest 56 addresses lower outer flank 55. Comparing tooth forms of FIGS. 4 and 5, flank 57 represents a chamfered surface, thinning the thickness of the crest 56.

Figure 6:
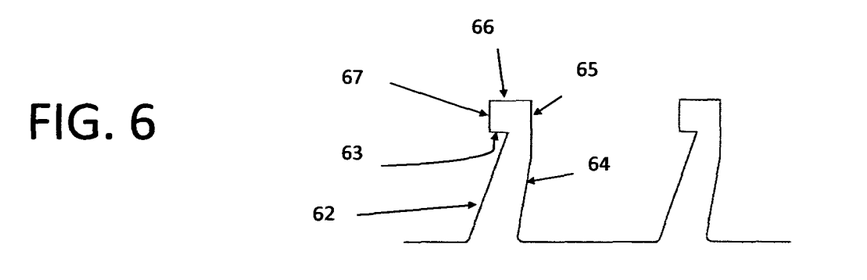
FIG. 6 shows a fourth tooth profile in section.
Figure 6A:
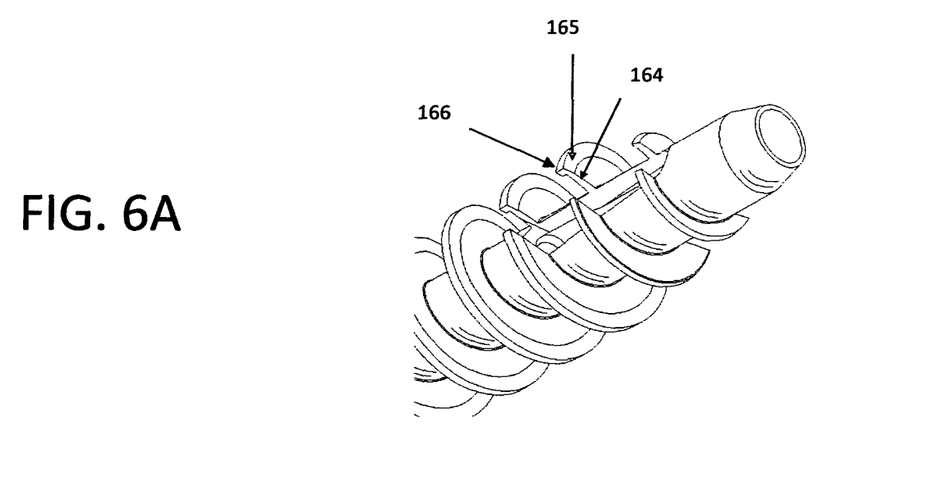
FIG. 6A shows one perspective of the FIG. 6 cutting flute.
Figure 6B:
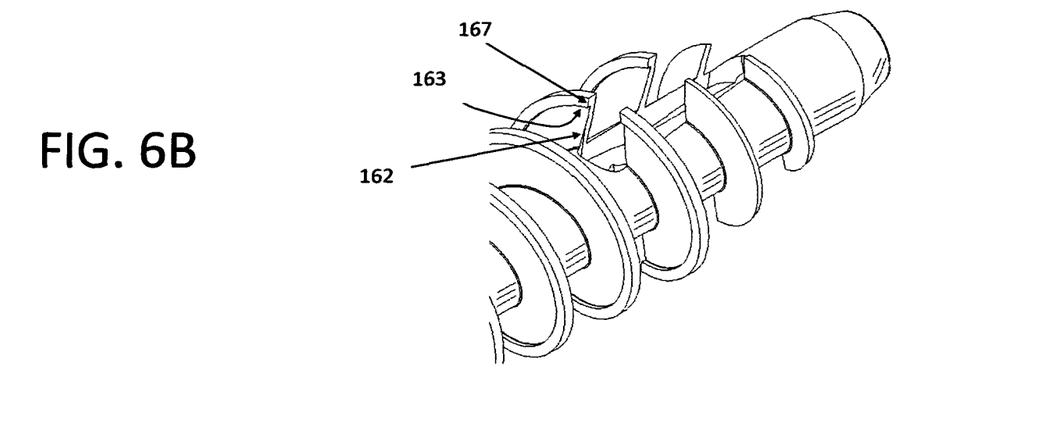
FIG. 6B shows a second perspective.

FIG. 6 reflects the upper, outer flank 63 is parallel to both the crest 66 and the fastener long axis 11. Consequently, a further outer facet 67 transitions between outer flank 63 and crest 66. Transition facet 67 parallels lower outer facet 65 and both are perpendicular to the long axis of the fastener. The dimension of transition facet 67 is variable.

Figure 7:
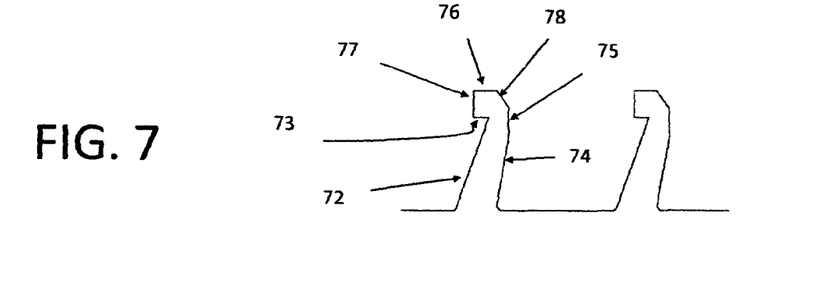
FIG. 7 shows a fifth tooth profile in section.

FIG. 7 includes a transition facet 77 similarly oriented and dimensional as facet 67, and the transition between a distal edge of the crest 76 and lower outer flank 75 enjoys a chamfer flank 78.

Figure 2A:
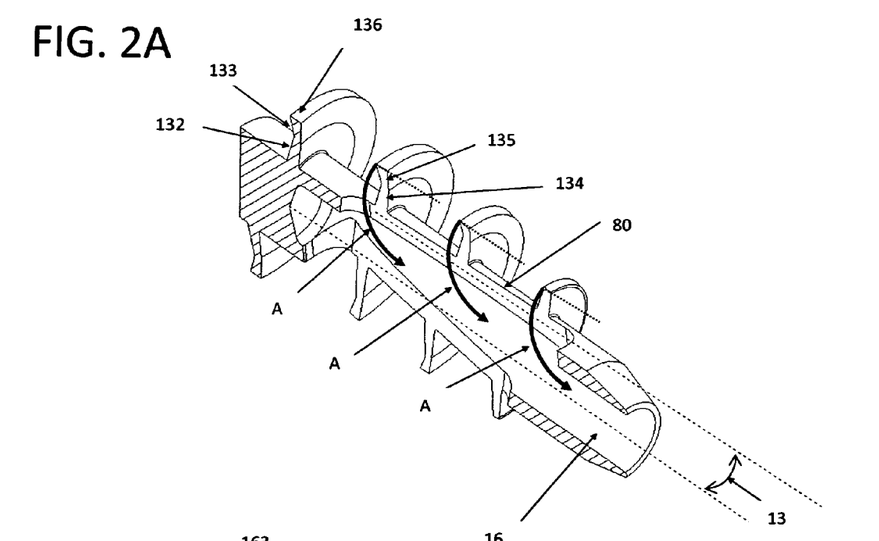
FIG. 2A shows a cutter directing bone shards along one path.
Figure 2B:
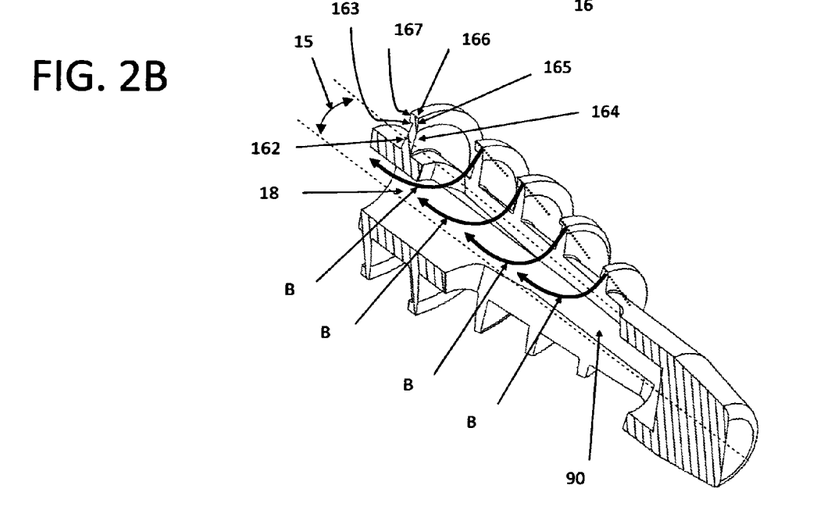
FIG. 2B shows a cutter directing bone shards along another path.

In each thread pattern shown in FIGS. 3-7, the active thread cutting geometry is shown in FIGS. 3A-7A and 3B-7B with details shown in FIGS. 2A and 2B providing bone shard transport into repository bores 80 or 90. While the FIG. 2A structure follows the FIG. 3 geometry and FIG. 2B follows the FIG. 6 geometry, none the less, it shall become clear the FIGS. 4, 5 and 7 threads are to be affected in the same manner.

Specifically, a hollow bore is created by drilling out the center of the fastener along the long axis 11 (FIG. 1). If the hollow bore is on the distal end, a drill penetrates a distance into the fastener from the distal end. Conversely, when the hollow bore is on the proximal end, the drill enters from the proximal end 4. Next, a broaching tool plunge cuts into the cylinder exterior at an angle offset from the long axis. The tooth pattern of FIG. 2A is achieved by cutting at a 5-10 degree angle 13—offset from the long axis 11 shown in FIG. 1. This results in edges on upper flanks 133 and 135 contacting bone before edges on lower flanks 134 and 135. This results in bone shards moving in the direction "A", down into hollow 80 and towards the distal end. The broaching tool, when forming the oval opening for the hollow 80 also removes material from the oval 83 at the distal end as shown by ramp 81 in FIG. 1. This sloped ramp 81, leading into the hollow, enhances the precision fit with the bone that is not removed. Sharp edges 82, circumscribing the remainder of the oval 83 assure a further precise fit.

FIG. 2B reflects the broaching tool oriented along a 5-10 degree offset (15) on the opposite side of the long axis 11. Please see FIGS. 1 and 6. FIG. 2B reveals the lower facets 164 and 165 will be the first to contact bone, sending bone shards along the arrow B, opposite from FIG. 2A. Shards advance downwardly into the hollow 90 and thence towards the proximal end. Thus, it is to be observed that by changing the chamfer of the teeth where the broaching tool removed material, the bone shard removal pattern can be modified to either the proximal or distal interior of the fastener.

Figure 4A:
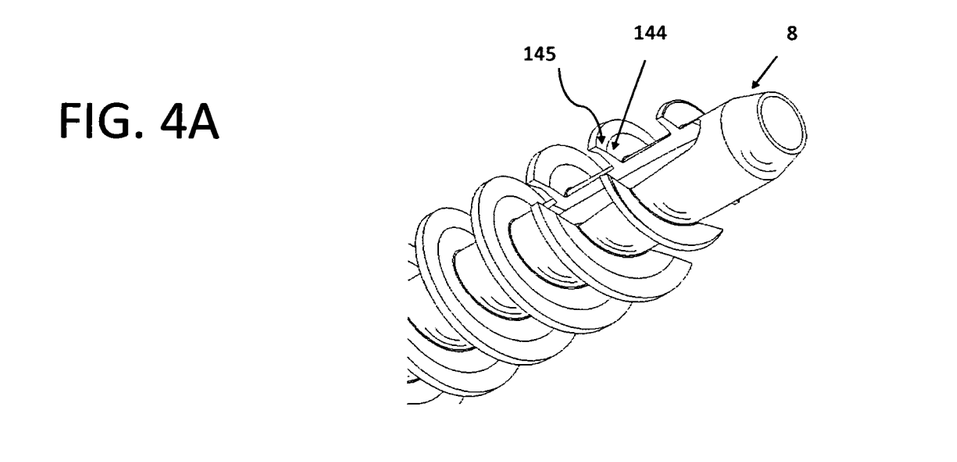
FIG. 4A shows one perspective of the FIG. 4 cutting flute.
Figure 4B:
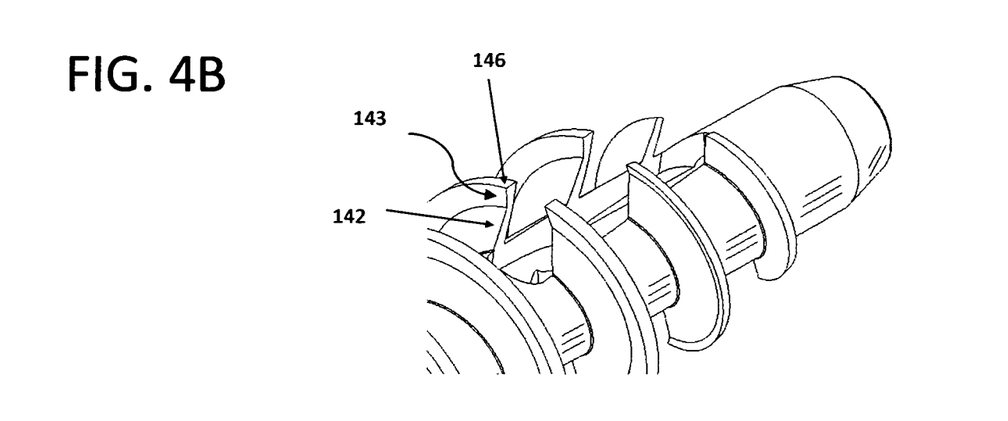
FIG. 4B shows a second perspective.
Figure 5A:
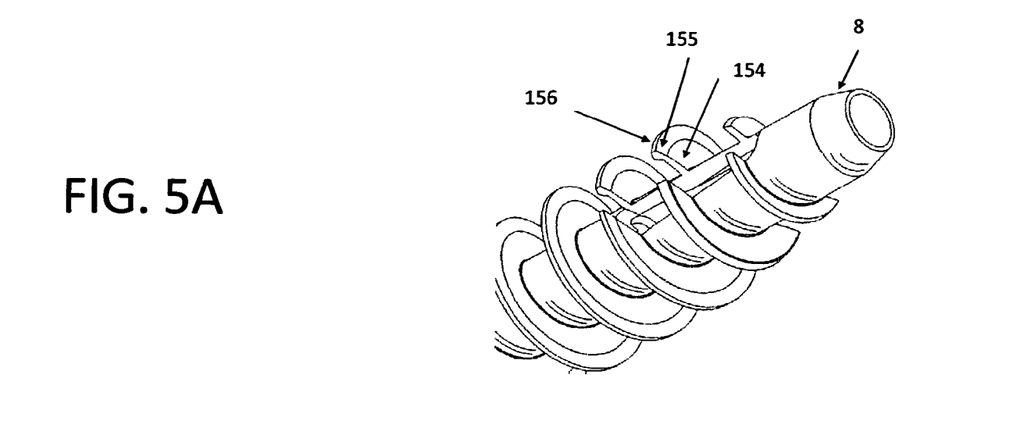
FIG. 5A shows one perspective of the FIG. 5 cutting flute.
Figure 5B:
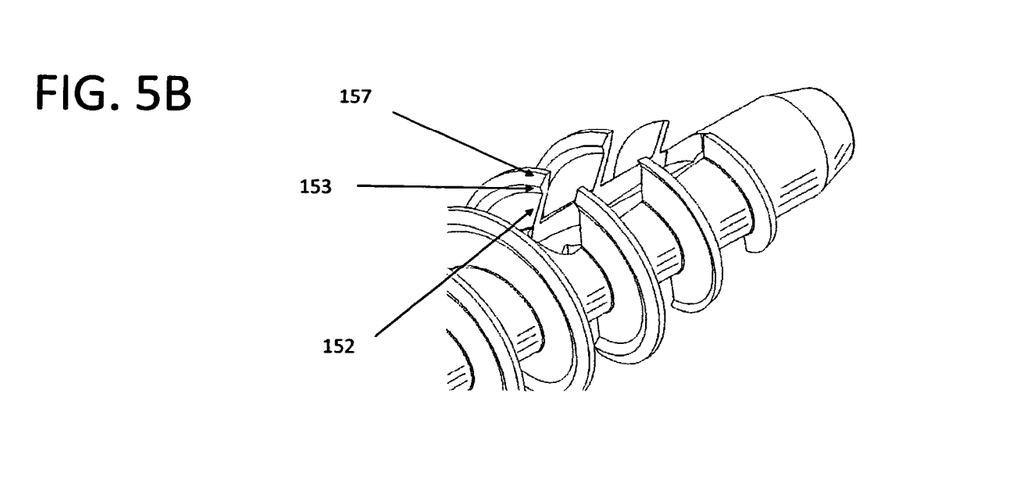
FIG. 5B shows a second perspective.
Figure 7A:
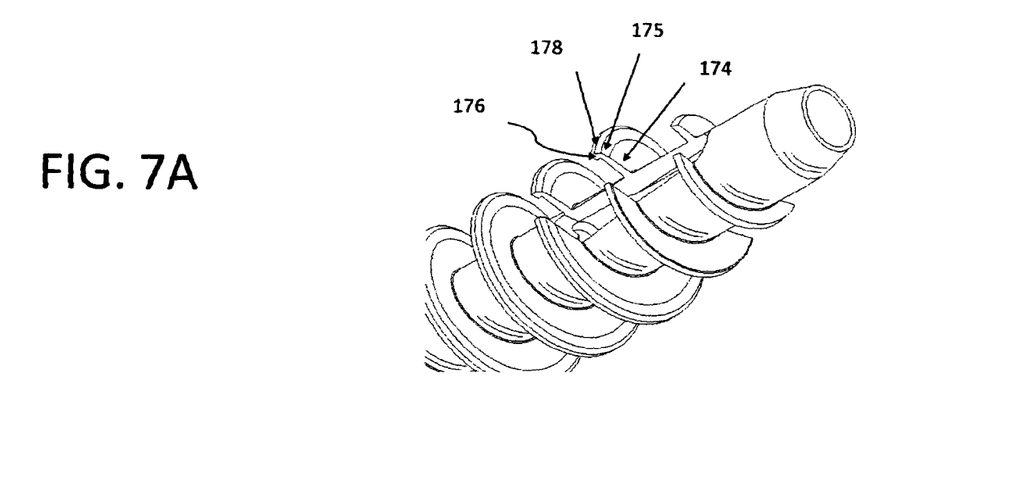
FIG. 7A shows one perspective of the FIG. 7 cutting flute.
Figure 7B:
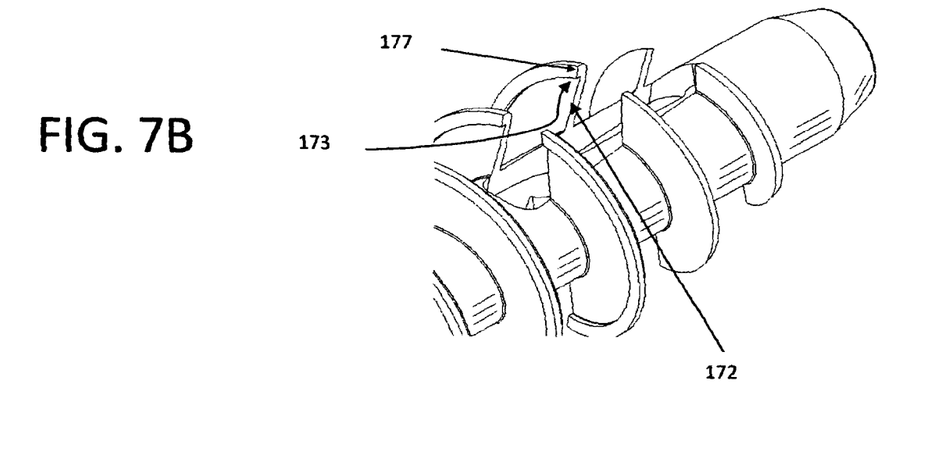
FIG. 7B shows a second perspective.

For example, in FIGS. 4A, 5A and 7A, if the leading edges of the cutter are to be 144, 154 and 174 for the lower root flanks 44, 54 and 74; and 145, 155 and 175 for the lower outer flanks 45, 55 and 75, then the FIG. 2B broaching technique is to be followed. Likewise, if the leading edges shown in FIGS. 4B, 5B and 7B are to be made effective, the FIG. 2A broaching step chamfers cutters 142, 143, 152, 153, 157, 172, 173 and 177 to lead the cutting.

Other variants are contemplated as part of this invention by the scope of the claims.

I claim:

1. A threaded fastener for embedment into bone, comprising:
    an elongated, cylindrical shaft having a distal end for embedment and a proximal end having means to rotate said fastener for advancement and retraction,
    a thread wound about said cylindrical shaft such that said thread spirals along at least a portion of said shaft, and space interposed between said spiral thread defines a cylindrical spiral,
    said thread having means for interlocking with adjacent bone into which said fastener is embedded defined by:
    a surface facing said proximal end defining an upper flank and formed from first and second facets, said first facet appearing planar when viewed in section and emanating from said cylindrical shaft and sloping downwardly, towards said distal end, said first facet terminating at said second facet, said second facet appearing substantially planar when viewed in section and sloping upwardly, towards said proximal end, a juncture between said first and second facets appearing as a sharp crease when viewed in section, said first and second facets collectively approximating a "V" shaped profile when viewed in section;
    a surface facing said distal end defining a lower flank and including a third facet emanating from said cylindrical shaft and declined towards said distal end such that an area below said third facet defined by a plane perpendicular to a long axis of said fastener and terminating at an outboard extremity of said third facet defines a material void constituting an undercut, and, a self-tapping cutter disposed adjacent said distal end having a contour which cuts a mirror image of said thread in the bone receiving said fastener whereby installation of said fastener experiences reduced resistance and said first, second and third facets interlock with said bone that was retained, uncut;
    whereby when said cylindrical shaft is rotated, bone shard is removed, and shard directional means are disposed within said cylindrical shaft to preclude bone shard entrapment within said threads, said shard removal not interfering with said threads thereby providing cleaner bone thread interface, said shard directional means having a length which is skewed relative to said long axis of said fastener.

2. The fastener of claim 1 including a pilot disposed at a distal extremity of said fastener such that said self-tapping cutter is interposed between said pilot and said thread, said pilot constraining said fastener to track a predrilled pilot hole.

3. The fastener of claim 2 wherein at least one portion of said cylindrical shaft is hollow and open adjacent said self-tapping cutter to receive bone shards therein, said hollow and open portion having an oval shape with a sloped ramp leading into said hollow and open portion, said hollow and open portion adjacent to said distal end skewed at an offset from said long axis of said fastener, said hollow and open portion oriented to direct bone shards in a precise direction axially.

4. The fastener of claim 3 wherein said hollow extends to said pilot, thereby defining an open distal end.

5. The fastener of claim 3 wherein said hollow extends to said proximal end, thereby defining open access from said proximal end to said self-tapping cutter, whereby, after installation, a drill, dimensioned to fit within said hollow may auger a quantum of bone shards away from said fastener and one or more substances selected from a group of substances which improve bone characteristics can be introduced into said hollow to migrate adjacent said fastener.

* * * * *

UNITED STATES PATENT AND TRADEMARK OFFICE
CERTIFICATE OF CORRECTION

| | | |
|---|---|---|
| PATENT NO. | : 9,526,547 B2 | Page 1 of 1 |
| APPLICATION NO. | : 13/815504 | |
| DATED | : December 27, 2016 | |
| INVENTOR(S) | : Reed | |

It is certified that error appears in the above-identified patent and that said Letters Patent is hereby corrected as shown below:

On the Title Page

The Assignee name is listed incorrectly. Please amend as follows:
Assignee: RTG Scientific Inc., Turlock, CA (US)

Signed and Sealed this
Tenth Day of September, 2019

Andrei Iancu
*Director of the United States Patent and Trademark Office*